United States Patent [19]

Grell et al.

[11] Patent Number: 4,535,885

[45] Date of Patent: Aug. 20, 1985

[54] PNEUMATIC SEALING APPARATUS

[75] Inventors: Karl-Heinz Grell, Ahrensburg; Heinz Krappitz, Reinbek, both of Fed. Rep. of Germany

[73] Assignee: B.A.T. Cigaretten-Fabriken GmbH, Fed. Rep. of Germany

[21] Appl. No.: 493,752

[22] Filed: May 11, 1983

[30] Foreign Application Priority Data

May 18, 1982 [DE] Fed. Rep. of Germany ....... 3219101

[51] Int. Cl.³ .......................... B65G 47/86; A24C 5/34
[52] U.S. Cl. ..................................... 198/695; 131/280; 277/80; 277/12
[58] Field of Search ....................... 209/535, 536, 537; 73/38, 41, 49.8; 277/80, 12, 152; 198/479, 480, 694, 695, 653

[56] References Cited

U.S. PATENT DOCUMENTS 3,386,281 6/1968 Menge et al. ...................... 73/49.8
3,677,068 7/1972 Schmermund ........................ 73/41
3,769,832 11/1973 Baier ....................................... 73/41
4,429,567 2/1984 Koch et al. ............................ 73/38
4,484,591 11/1984 Wahle et al. ........................ 131/280

FOREIGN PATENT DOCUMENTS 2150186 4/1973 Fed. Rep. of Germany .
2462551 8/1977 Fed. Rep. of Germany ...... 198/480
3110550 9/1982 Fed. Rep. of Germany ...... 198/480

Primary Examiner—V. Millin
Assistant Examiner—H. Macey
Attorney, Agent, or Firm—Roylance, Abrams, Berdo & Goodman

[57] ABSTRACT

The opening and closing of a sealing arrangement for the connection of a cylindrical body with an inside flange elastically deformed during opening, is controlled by a magnetic operating device, the axially opposite parts of which are disposed on a holding body attached to the sealing arrangement and along a control path past which the sealing arrangement moves.

16 Claims, 4 Drawing Figures

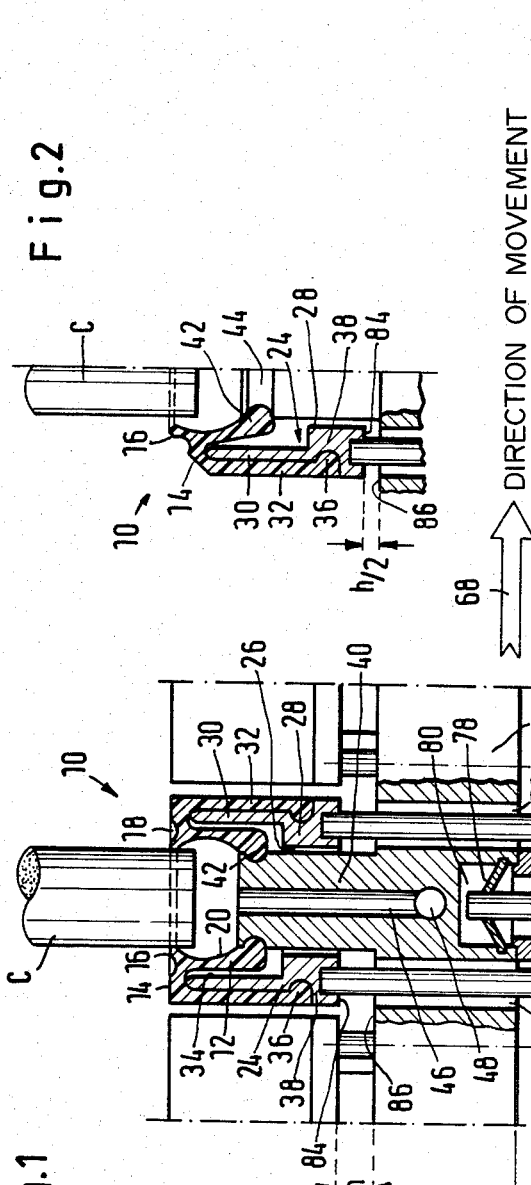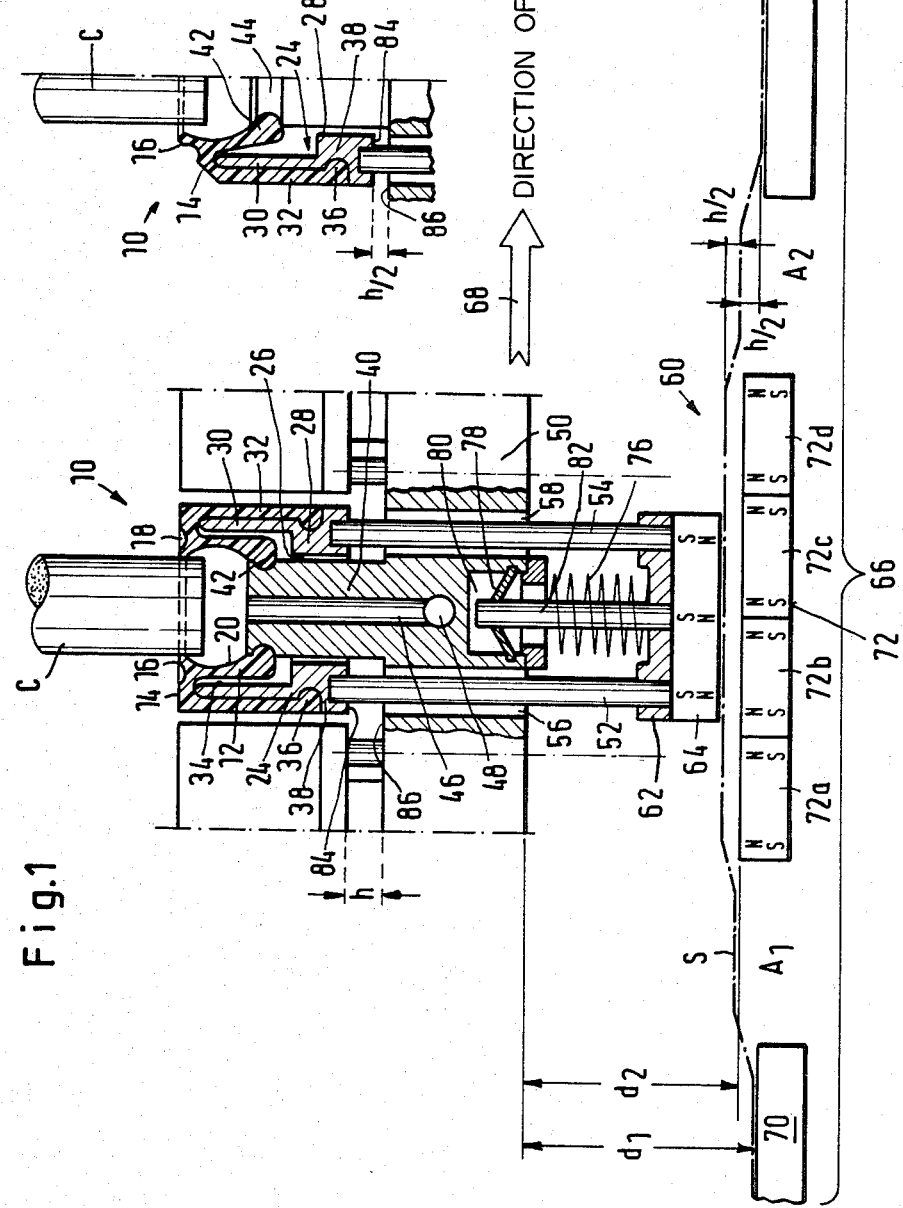

PNEUMATIC SEALING APPARATUS

BACKGROUND OF THE INVENTION

In the process of manufacturing cigarettes, it is necessary to test each cigarette and, if a flaw is detected, the flawed cigarette must be rejected. In this testing process, it has become standard to connect a test air line to the end of each cigarette for a very short interval of time during which air under pressure is injected into the cigarette and certain measurements are made. A sealing arrangement for this purpose is described in copending U.S. patent application Ser. No. 469,895, Krappitz et al., filed Feb. 25, 1983. That apparatus permits forming a seal at the end of a cylindrical body, particularly a cigarette, in such a way that a test air line is coupled in a precisely coaxial, concentric arrangement with the cigarette with a perfect seal.

The arrangement described therein avoids the disadvantages of previously known pneumatic test methods and apparatus as they are described and shown, for example, in German OS 2,150,186, OS 2,324,055 and OS 2,753,835.

As discussed in connection with the background of the previously mentioned copending application, the previously used devices involved essentially cylindrical or slightly conical sealing bodies with an axial bore and a connecting or seaing surface which is concave somewhat in the manner of a cup or ball, or the interior of a trumpet mouthpiece, the larger diameter thereof being somewhat larger than the end of the article being tested. The sealing surface of such an arrangement is moved up to the end of a cigarette and is pressed against the end so that the end of the cigarette is slightly radially compressed. Unfortunately, in such devices it is entirely possible for their to be off-center contact between the sealing body and the cigarette. Misalignments or imprecisions in this connection may not be balanced out so that more or less serious impairments of the sealing can occur.

The arrangement discussed in Ser. No. 469,895, disclosed a sealing arrangement which overcame these disadvantages, permitting the outer surface of the cylindrical end of the cigarette to be enclosed in a perfect sealing arrangement in which the end of the cigarette is not impaired in any way. Furthermore, the principle applied in that arrangement automatically guarantees centering and perfectly reliable and even sealing.

The apparatus disclosed therein operates in such a way that an inner flange of a sealing body is stretched open and enlarged and then is allowed to relax and close around the end of the cigarette. The sealing arrangement can be moved in its open position to the end of the cigarette or the like which is to be sealed and then is allowed to close so that the end of the cigarette is encompassed until the seal is broken by again stretching open the sealing body and moving it away from the end of the cigarette.

In order to carry out the opening and closing movement, a holding body engaging the outside flange of the sealing body is moved axially back and forth with respect to the sealing body support. The means for the mechanical drive and control of the opening and closing movement of the seal proposed in Ser. No. 469,895 comprises a guide arrangement with a cam path along which spring forks travel, the legs of the forks engaging recesses in the holding bodies. While this apparatus is capable of functioning in a very suitable fashion, because of the fact that it is an entirely mechanical device and involves a degree of friction between relatively moving parts, it is unavoidable that a certain amount of wear and, therefore, degeneration of the mechanical operation of these components occurs.

BRIEF DESCRIPTION OF THE INVENTION

Accordingly, an object of the present invention is to provide a driving and control means for opening and closing an elastic seal in an automated production apparatus, especially for the production of cigarettes, which runs at a very high speed but which nevertheless operates reliably for testing each individual article so that defective articles can be separated out.

A further object is to provide such an apparatus in which mechanical contact of parts abrading each other is avoided.

Briefly described, the invention includes an apparatus for controlling the deformation of the open end of a cylindrical sealing body between a closed position to momentarily enclose and seal around the end of a cylindrical article to be pneumatically tested and a deformed open position, the sealing body being mounted on a support member and attached to a holding body at the other end from the support member so that relative axial movement between the support member and holding body causes the opening and closing, the apparatus comprising means for carrying and moving said sealing body, said support member and said holding body along a travel path which is generally perpendicular to the axis of said sealing body, one of said support member and said holding body being axially movable relative to said carrying means and the other being fixed thereon; fixed control means for controlling relative movement between said support member and holding body, said control means being arranged along a control path generally paralleling said travel path; a first magnetic member carried by the movable one of said holding body and said support member and extending toward said control means; and said control means comprising second and third magnetic members having magnetic properties differing from each other arranged along segments of said control path such that said first magnetic member is differently attracted and repelled thereby, causing axial movement of said first member and the movable one of said support member and holding body and concurrent opening and closing of said sealing body, at least one of said first, second and third magnetic members being a permanent magnet.

The control which operates in the present invention is solely on the basis of magnetic forces or magnetic field forces for opening and closing the elastic seal and is thereby distinguished from the mechanical control in which frictional contact between the spring arms and cam path exists, the present arrangement nevertheless involving relatively low technical and financial expenditure.

As will be seen from the following detailed discussion, a portion of the control arrangement which is movable along an axially opposite control path and seated on the holding body can be a permanent magnet or a magnetizable part made of ferromagnetic material.

BRIEF DESCRIPTION OF THE DRAWINGS

In order that the manner in which the foregoing and other objects are attained in accordance with the invention can be understood in detail, particularly advantageous embodiments thereof will be described with reference to the accompanying drawings, which form a part of this specification, and wherein:

FIG. 1 is an axial section through a pneumatic sealing and control apparatus in accordance with the invention in the closed position, the figure also including a developed, "unrolled" illustration of a control path of the control arrangement for opening and closing the sealing apparatus;

FIG. 2 is a partial sectional view of a portion of the sealing arrangement of FIG. 1 in an intermediate, half-open position;

Figure 3:
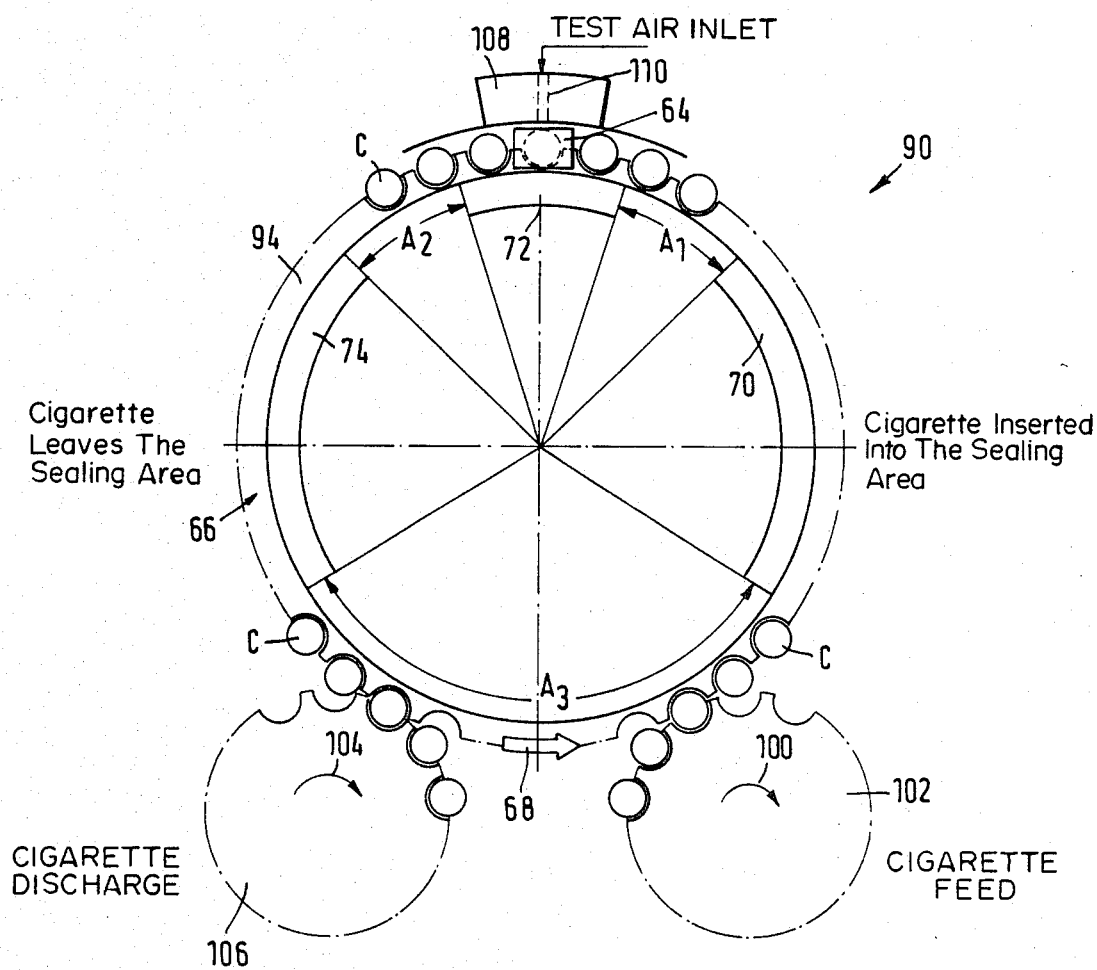
FIG. 3 is a schematic end elevation of a pneumatic cigarette test arrangement incorporating the sealing and control apparatus in accordance with the invention to illustrate the magnetically cooperating components of a preferred embodiment of the control arrangement.

Referring first to FIG. 1, it will be seen that the basic sealing arrangement includes an essentially hollow cylindrical sealing body 12 which generally corresponds to the apparatus disclosed in application Ser. No. 469,895, and is formed from rubber or a similar elastomeric material. At its free end, the sealing body 12 has a flange 14 projecting radially outwardly and a flange 16 projecting radially inwardly in essentially the same plane. The inside flange 16 forms the actual seal for connection to a cigarette C or a similar cylindrical body such as a cigarello, a cigar, a filter body or the like. Between the inside flange 14 and the outside flange 16 there is an annular groove 18 formed in the front face of the sealing body, the groove being provided to improve the mobility of the flange 16 to assist it in performing its function as a sealing lip during opening and closing of the seal.

In a preferred embodiment of the invention, the inner cylindrical jacket surface of the sealing body 12 is formed with a barrel-like shape having an annular surface 20 which is outwardly concave. This characteristic is advantageous particularly because it permits an especially wide opening of the sealing lip 16, as will also be seen in FIG. 2, and thus improves the secure seizing of the end of a cigarette or other article.

A holding body 24 axially engages the outside periphery of the flange part 14, the holding body having a bottom section 28 with a central axially extending passage 26, and a hollow cylindrical body portion 30 extending axially therefrom to the underside of flange 14. The sealing body includes an outer hollow cylindrical portion 32 which is connected to the outer periphery of flange 14, is radially spaced from body 12 leaving an annular space 34 and which surrounds body portion 30 and lies radially outwardly of body 12.

The outside hollow cylinder 32 is made of the same elastic material as the sealing member and is preferably unitarily formed so as to extend from the outside edge of the flange, as shown, and is pulled over the hollow cylinder 30 of holding body 24, extending into the annular space 34. The assembly of the holding body and the sealing body is facilitated when the inside diameter of the cylindrical part 30 of the holding body 24 is somewhat larger than the outside diameter of the hollow cylindrical section 12 of the sealing body. The fact that annular space 34 remains, in part, after the assembly of the sealing body 10 on the holding body is an advantage for unimpeded opening and closing movement of the sealing body. From this it will be seen that axial movement of body 24 relative to member 40 in a downward direction (referring to the orientation of FIG. 1) carries with it portion 32 and flange 14, deforming and stretching flange 16 and causing the circular opening within flange 16 to enlarge, thus permitting insertion or removal of articles C.

A rounded annular flange or bead 36 projects radially inwardly from the distal end, the end facing away from flanges 14, 16, of outside cylinder 32 of the sealing body. In its assembled state, bead 36 matingly engages with a correspondingly shaped peripheral annular groove in the outside jacket of the base portion 28 of holding body 24 and restrains the outside portion from axial movement relative to the holding body.

In a somewhat similar fashion, the distal end of the hollow cylindrical sealing body 12 distant from flange portions 14, 16, is provided with a radially inwardly extending flange or bead 42 which engages a peripheral annular groove 44 at the end of supporting body 40 which extends through the central bore 26 of holding body 24. The bead 42 can be formed so that it is considerably stretched when it is placed on body 40, thereby forming an air-tight connection of the sealing body to the supporting body 40.

This arrangement guarantees a secure connection between the sealing, holding and supporting bodies even during the deformation of the sealing body 12 during opening and closing of the seal as will be described.

The end portion of the foot part 28 of holding body 24 has an outer surface which is the same diameter as the outside surface of the hollow cylinder 32, thus forming a continuous cylindrical outside surface for the sealing arrangement. The supporting body 40 has an air passage channel including portions 46 and 48 to which can be connected a test air feed line. In the embodiment shown, the test air channel of the supporting body 40 has a portion of bore 46 leading coaxially into the hollow cylindrical sealing body 12 and a second portion 48 of the bore extending radially and connecting with passage 46 at a right angle. The radial bore portion 48, at the same time, lies in a carrier 50 which is fixedly attached to supporting body 40 and which can be unitarily molded therewith, this combination forming one of a series of successive sealing arrangements which are closely spaced from each other.

Connecting rods 52 and 54 are attached to holding body 24 on the surface facing away from sealing body 12 and extend with radial clearance through axially extending bores 56, 58 in carrier 50, the other ends of the connecting rods being coupled to a magnetic operating device indicated generally at 60 which is located on the side of the carrier axially opposite from the sealing body and serves for the forced control of the opening and closing movement of the seal by axial reciprocating movement of the holding body 24 relative to the support body 40.

In the embodiment according to FIG. 1, a portion of the magnetic control arrangement 60 includes an axially magentizable permanent magnet 64 which is attached by a mounting plate 62 to the ends of the connecting rods 52, 54.

Additional components of the control arrangement 60 are shown disposed on sections along a locally fixed control path axially opposite the permanent magnet 64, a section 66 of the control path being shown in FIG. 1 in an "unrolled" representation, the apparatus being arranged such that the sealing apparatus seated on carrier 50 is moved past in the direction indicated by arrow 68. As illustrated in FIG. 1, the fixed portion of path 66 includes, in sequence, a non-magnetic and non-magnetizable interval A1, an axially magnetized permanent magnet section 72 which is shown opposite the permanent magnet 64 connected to holding body 24 of the sealing arrangement 10, a section A2 which, like section A1, is non-magnetic and non-magnetizable interval, and a section 74 which is ferromagnetic, like section 70.

The sections 70 and 74 of the control path are studded, for example, with elongated, bar- or strip- shaped parts made of steel such as, for example, Steel 37, or with some other ferromagnetic material.

The permanent magnet section 72 of the path is formed, for example, by a successive longitudinal row of permanent magents 72a, 72b, 72c and 72d, all of which have their magnetic poles arranged in the same direction. The arrangement of parts 70-72 of the control path is made, according to the illustration, in such a way that the axial distance d1 between sealing arrangement 10 and the ferromagnetic sections 70 and 74 of the path are somewhat larger than the axial distance d2 between sealing arrangement 10 and the permanent magnetic section 72 of the path. The distances d1 and d2 are shown as existing between the side of the carrier 50 facing away from the sealing arrangement 10 and the pertinent sections of path 70, 74 or 72.

In this embodiment of the invention, a relatively weak compression spring 76 lies axially between the mentioned reverse side of the carrier 50 or of the supporting body 40 and the mounting plate 62 coupled to holding body 24. Compression spring 76, which can be a helical spring, biases the sealing body 12 in a direction contrary to its elastic tendency into a half-opened, middle or intermediate position. This intermediate position, shown in FIG. 2, will be assumed to be the rest or starting position whenever no magnetic fields or magnetic forces of the control path 66 repel or attract permanent magnet 64 and, thus, do not act on body 24. The middle starting position therefore exists automatically whenever the sealing arrangement 10, during its movement along path 66, is located in the areas of non-magnetic and non-magnetizable intervals. A1, A2 between the sections of the path 70-72 and 74.

For the purpose of centering holding body 25 during its forced axial reciprocating movement, a centering arrangement including a membrane-like plastic ring 78 which extends between the inside wall of an axially extending cylindrical recess 80 in the bottom of supporting body 40 and a centering rod 82 which protrudes concentrically into the recess from mounting plate 62, the centering rod also comprising a guide for compression spring 76.

The arrangement shown is particularly advantageous because the compressing spring 76 and the spring membrane 78 act in axially opposite directions during the pre-tensioning and centering of the holding body 24 and, thus, of the entire sealing arrangement, and operate to support each other.

The pattern of the axial movement of the permanent magnet 64 and holding body 24 during opening and closing of the seal during the movement of the sealing arrangement 10 relative to control path 66 is indicated in FIG. 1 by a dash-dot line or control curve S. As indicated relative to that line, the total extent of axial movement, or lift, of the sealing arrangement 10 during opening and closing of the seal, is the dimension h. The opening stroke caused by attraction of permanent magnet 64 attached to holding body 24 to the ferromagnetic element 70 or 74 of the control path 66 is limited by stops in order to safely preclude any contact between the permanent magnet 64 and the oppositely lying surfaces of the control element 70 or 74 during the relative movement therebetween. These stroke limiting stops, in the embodiment shown, are advantageously formed simply by opposing surfaces 84 and 86, lying axially opposite each other, on the bottom of holding body 24 and on the face of carrier 50.

Figure 4:
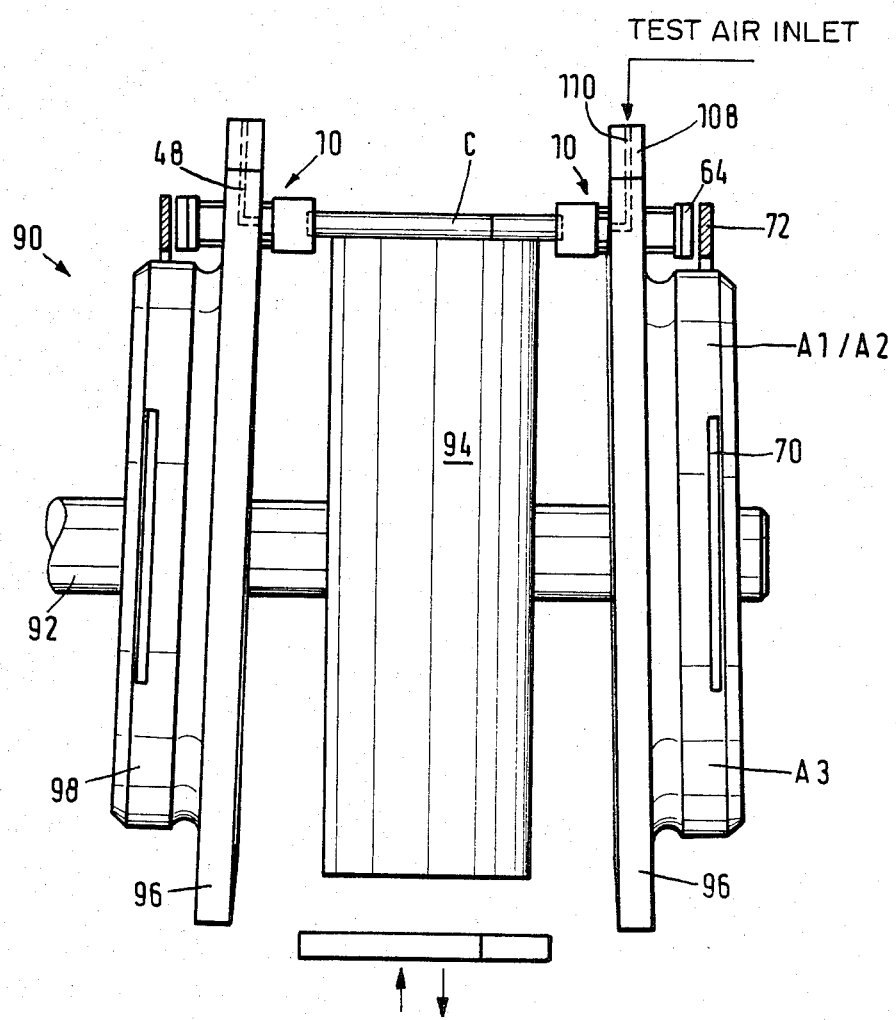
FIG. 4 is a side elevation of the apparatus according to FIG. 3.

FIGS. 3 and 4 show an overall view of a more complete apparatus incorporating the present invention for pneumatic testing of cigarettes, the same reference numbers for the parts previously described being used in these figures.

The apparatus indicated generally at 90 has a customary testing drum 94 which is rotatable on a shaft 92 and also includes disc-shaped annular members 96 which are inclined relative to the axis of shaft 92 on axially opposite sides of the testing drum at the same distance, members 96 being mirror-image symmetrical with respect to the central plane of the drum. Members 96 correspond to the carrier 50 shown in FIG. 1 on which a succession of sealing arrangements 10 are disposed, facing each other and axially aligned with each other, the sealing arrangements being uniformly circularly spaced about the periphery of the apparatus.

Bearings for the slightly inclined test rings 96 are disposed transversely in relation to the bearing axis of shaft 92 of the test drum 94 and are accommodated, for example, in fixed bearing carriers 98 with which the entire testing arrangement 90 can be mounted on a machine which is conventional in the cigarette industry.

The basic arrangement of a test drum with test rings placed transversely thereto, which are together rotatably connected with the drum, is known, per se. This arrangement permits a particularly simple relative movement between the cigarettes, which are carried by the test drum 94, and the sealing arrangements which, in open position, are moved with the sealing flange extended, toward the end of the cigarette to be seized, such that, upon closing of the seal, the end is encompassed in a sealing manner by the relaxed sealing flange 16.

FIG. 3 diagramatically illustrates how the cigarettes which are to be individually tested are delivered from a cigarette feed drum 102, rotating in the direction of arrow 68, and after testing are taken again from the drum by way of a cigarette output drum 106 revolving in the direction of arrow 104. It is also known to hold the individual cigarettes, with the help of vacuum, and convey them in a controlled manner between axis-parallel receiving grooves in the drum such as 68, 102 and 106.

The control path 66, mounted in a locally fixed manner, according to FIG. 4, lies in parallel with one of the test rings 96 mounted transversely with respect to drum 94 in an annular zone including the associated bearing carrier 98. As will be recognized from these figures, the control paths 66 are bent upon themselves in a circular, endless path, each such control path having the angular sections 70, A1, 72, A2, 74 which are shown in the unrolled illustration of FIG. 1, and also having an additional non-magnetic and non-magnetizable section A3 lying between sections 70 and 74 in the area of a sector which is occupied by the feed and removal drums revolving on opposite sides of the lower apex of testing drum 94, section A3 occupying approximately one-third of the path periphery. The sections of the path axially opposite the magnet 64 of the sealing arrangements 10 are shown in FIG. 3, only for reasons of clarity, on a smaller diameter of the path.

The individual sealing arrangements 10 are mounted on the oppositely lying test rings 96 at a slanting angle with respect to those test rings, the angle being chosen such that they come into axis-parallel alignment with the axis 92 of drum 94 in the upper apex region of the test drum, that being the region in which the axial distance between the test rings is smallest.

In the diametrically opposite lower sector of the drum, the distance between the axially opposite sealing arrangements is greater than the axial length of the cigarettes to be tested which permits the cigarettes during feed-in to be placed between the oppositely lying sealing arrangements into a holding groove of the drum, and also permits removal of the cigarette at drum 106, without interference between the ends of the cigarettes and the sealing arrangements. In the embodiments shown in FIGS. 1 and 2, the sealing arrangement during the feed-in and output of the cigarettes is located in the non-magnetized or magnetizable area A3 in its half-open or intermediate position as illustrated in FIG. 2.

During travel over the section 70 of the control path (FIG. 3) the seal is completely opened by magnetic attraction between the magnet 64 of the holding arrangement and the ferromagnetic material, the stops 84, 86 acting to prevent any contact of the ferromagnetic strips of material 70 with magnet 64. In this area, the cigarette ends are inserted into the sealing bodies 20 which, at that point, are opened wide. When the bodies pass into the non-magnetic section A1, each sealing body returns to its half-open intermediate position. However, upon reaching section 72, magnet 64 is moved by a repelling action of the oppositely magnetized section 72 into its closed position in which the seal encompasses the end of the cigarette tightly as illustrated in FIG. 1. At the upper apex of the test drum, a test air connection to the ends of the cigarette is produced through a test channel 48, 46 which is coupled to a source of test air which is provided through a sliding block 108 having an air passage bar 110, the passages being aligned at the apex as illustrated in FIGS. 3 and 4.

When each sealing arrangement reaches the sector A2 of the path the sealing arrangement is again not influenced by magnetic forces and resumes its half-open intermediate position shown in FIG. 2 and then is completely opened during passage through the section 74 of the path by magnetic attraction between the ferromagnetic material strip 74 and magnet 72 in order to facilitate emergence of the cigarette ends from the oppositely disposed sealing arrangements. As each sealing arrangement again reaches sector A3, the sealing arrangements are axially spaced from the cigarette ends and the cigarettes themselves are removed by drum 106.

The interposition of a section A3 without magnetic influence on magnet 64 of the sealing arrangement 10 has the primarily advantage of a saving of material without impeding the feed or delivery of the cigarettes which, in this area, could occur without difficulty in the axial interval between the opposite sealing arrangements 10. However, should unexpected problems arise in this region during the seizing of the cigarettes, it would be possible, in a modified embodiment, to omit the gap A3 and, alternatively, provide a section formed preferably, in one piece with the sections 70 and 74, made of ferromagnetic material.

Initial experiments with a magnetic control arrangement in accordance with the invention for the opening and closing movement of the sealing arrangement 10 have convincingly, showed excellent operating results. It also became apparent that a total lift h of the sealing arrangement 10 of about 4 mm is quite sufficient as are the partial lifts illustrated in FIG. 1. The opening diameter of the inside flange 16 of the sealing body 12 forming the actual seal amounted to about 9.8 mm in the area of the ferromagnetic section of path 70 or 74, and the half-open position had a diameter in the sections A1, A2, A3 of about 8.8 mm. In the closed position in which the cigarettes are located in the area of section 72, the diameter is about 7.8 mm. Cigarettes with an 8 mm diameter were tested and it should be understood that fluctuations in the diameter of cigarettes produced by fully automatic machines are consistently smaller than the difference to the selected closing diameter of the sealing arrangement so that, during automatic testing, a perfect connection to each cigarette is insured and, because the sealing bodies are made of plastic, molded parts can be produced with high precision.

The deformation apparent from FIGS. 1 and 2 is facilitated by the outwardly bulging barrel shape of the annular zone of the inside jacket surface 20 of the sealing body 12 merging uniformly into the inner flange 16, but otherwise the arrangement corresponds in principle to the previously mentioned application Ser. No. 469,895, wherein the inner sealing flange 16, which is released during closing and stretched during opening, insures a perfect sealing and closing relationship of the seized end of the cigarette.

Parts which according to the invention are permanently magnetic or ferromagnetic and disposed on sections of the control path determined in accordance with the desired sequence of opening and closing movements of the seal at the same time, by attraction or repulsion of the component seated on the holding body, cause the forceably controlled axially reciprocating movement of the holding body carrying the sealing body and, thus, the desired opening or closing movements of the actual seal formed by the inside flange of the sealing body which seizes the end of the cigarette. In each case, the arrangement is made such that a contact of the part seated on the holding body and of a part on the control arrangement seated on the axially opposite control path, if need be, is prevented as a result of axial limit stops of the opening and closing movement of the seal. Basically, variable control movements are possible for carrying out the opening and closing movements in various forms of the invention.

For example, the sealing arrangement pre-tensioned by a built-in pre-tensioned spring, can be opened by a fraction of a part of the control arrangement seated on the holding body to the part provided on a fixed section of the control path. In this embodiment, a part of the control arrangement consists of a permanent magnet while the other axially opposite part consists of a ferromagnetic material such as iron or steel. The desired mode of operation of this embodiment of the invention is independent of whether the permanent magnet part is attached to the holding body and the ferromagnetic part to the control path or vice versa. In the case of an arrangement where the magnetizable ferromagnetic part of seated on the holding body, the magnetic part disposed on the control path can also be an electromagnet rather than a permanent magnet.

In another embodiment of the invention, the sealing arrangement can be pre-tensioned into its open position and may be closed by an axially magnetized permanent magnet seated on the holding body is moved past an axially magnetized permanent magnet of opposite polarity existing on a section of the control path so that the sealing arrangement is shifted by the holding body repelled by the magnetic forces, thereby moving it in its closing direction.

Particularly precies control with an advantageously short operating stroke of the sealing arrangement is guaranteed with an embodiment of the invention in which a pre-tensioned spring acting in the opening direction of the seal lies between the holding body and the supporting body and holds the sealing body in the half-open position as long as no magnetic influences act on the holding body. This is the case whenever an axially magnetized permanent magnet seated on the holding body during its movement relative to the control path in the area of extended gaps is located between ferromagnetic sections of the path and permanent magnetic sections of the path succeeding each other at a distance and axially oppositely poled relative to the magnet of the holding arrangement. A further development in which the axial distance between the sealing arrangement and the ferromagnetic section of the path for opening the seal is greater than the axial distance between the sealing arrangement and the permanent magnetic section of the path for closing the seal permits high precision of control with relatively adjusting forces and short operating strokes.

While certain advantageous embodiments have been chosen to illustrate the invention, it will be understood by those skilled in the art that various changes and modifications can be made therein without departing from the scope of the invention as defined in the appended claims.

What is claimed is:

1. An apparatus for controlling the elastic deformation of the open end of a cylindrical sealing body between a closed position to momentarily enclose and seal around the end of a cylindrical article to be pneumatically tested and an enlarged open position, the sealing body mounted on a support member and attached to a holding member at the other end from the support member so that relative axial movement between the support member and holding member causes the opening and closing, the apparatus comprising:
   means for carrying and moving said sealing body, said support member and said holding member along a travel path which is generally perpendicular to the axis of said sealing body, one of said members being axially movable relative to said carrying means and the other member being fixed thereon;
   fixed control means for controlling relative movement between said support member and holding member, said control means being arranged along a control path generally paralleling said travel path;
   a first magnetic device carried by the movable one of said members and extending toward said control means; and
   said control means comprising second and third magnetic devices having magnetic properties differing from each other arranged along segments of said control path such that said first magnetic device is differently attracted and repelled thereby, causing axial movement of said first device and the movable member and concurrent opening and closing of said sealing body, at least one of said first, second and third magnetic devices being a permanent magnet.

2. A apparatus according to claim 1 wherein said first magnetic device is a permanent magnet and said holding member is movable and is coupled to the opening end of said sealing body.

3. An apparatus according to claim 2 wherein said first and second magnetic devices are axially magnetized permanent magnets having their like poles facing toward each other.

4. An apparatus according to claim 3 wherein an arcuate portion of said path is a ferromagnetic material separated from a permanent magnetic portion thereof by an angular distance,
   and wherein the axial distance between said support member and said ferromagnetic material is greater than the distance between said support member and said permanent magnetic portion,
   said apparatus further comprising a spring acting between said support member and said holding member and urging said sealing body toward an intermediate position.

5. An apparatus according to claim 4 and including stop surfaces on said holding member and said support member for limiting the axial movement in the direction of opening said sealing body.

6. An apparatus according to claim 2 wherein an arcuate portion of said path is a ferromagnetic material separated from a permanent magnetic portion thereof by an angular distance,
   and wherein the axial distance between said support member and said ferromagnetic material is greater than the distance between said support member and said permanent magnetic portion,
   said apparatus further comprising a spring acting between said support member and said holding member and urging said sealing body toward an intermediate position.

7. An apparatus according to claim 6 wherein a segment of ferromagnetic material is provided on both sides of said permanent magnet portion.

8. An apparatus according to claim 2 wherein said sealing body and said first magnetic device are on axially opposite sides of said means for carrying and moving.

9. An apparatus according to claim 8 and including axially extending holding rods between said holding member and said first magnetic device, said means for carrying having clearance holes for said rods.

10. An apparatus according to claim 9 and including centering means for guiding the axial motion of said holding member, said centering means acting between said holding member and said support member.

11. An apparatus according to claim 2 wherein said holding member comprises a generally tubular member having an open end,
   and wherein said sealing body includes a generally cylindrical inner portion having a closed end abutting said support member, an open end and a generally cylindrical outer skirt radially spaced from said inner portion,
   said tubular member of said holding member being received within said skirt and outside of said inner portion.

12. An apparatus according to claim 1 wherein said first and second magnetic devices are axially magnetized permanent magnets having their like poles facing toward each other.

13. An apparatus according to claim 1 and including axially extending holding rods between said holding member and said first magnetic device, said means for carrying having clearance holes for said rods.

14. An apparatus according to claim 13 wherein said support member includes an axially inwardly extending recess, said centering means including a rod coupled to said holding member and an annular membrane-like disk surrounding said rod and received in said recess, said disk being slidable to guide said rod.

15. An apparatus according to claim 1 and including a rotatable test drum having peripheral means for receiving and carrying a plurality of articles to be tested, said means for carrying having a plurality of sealing members, support members and holding bodies uniformly peripherally spaced thereon, means for rotatably mounting said means for carrying for rotation in a plane inclined relative to the plane of rotation of said drum, said drum and means for carrying being spaced apart such that a sealing body and an article carried by said drum engage at one location in the revolution thereof.

16. An apparatus according to claim 1 wherein said sealing body includes an inner surface of revolution which is concave outwardly in cross section.

* * * * *